(12) United States Patent
Shin et al.

(10) Patent No.: US 6,207,441 B1
(45) Date of Patent: Mar. 27, 2001

(54) METHOD FOR PRODUCING DOCOSAHEXAENOIC ACID (DHA) USING PSEUDOMONAS SP. YS-180

(75) Inventors: Yong Seo Shin, Iksan; Il Hwan Ryu, Jongsun-kun, both of (KR)

(73) Assignee: Seong Gu Ryu (KR)

( * ) Notice: Subject to any disclaimer, the term of this patent is extended or adjusted under 35 U.S.C. 154(b) by 0 days.

(21) Appl. No.: 09/458,765

(22) Filed: Dec. 10, 1999

(30) Foreign Application Priority Data

Apr. 20, 1999 (KR) .................................................. 99-14064

(51) Int. Cl.$^7$ ............................... C12N 1/20; C12P 7/64; C12P 1/04

(52) U.S. Cl. ........................ 435/253.3; 435/134; 435/170

(58) Field of Search ................................ 435/253.3, 134, 435/170

(56) References Cited

PUBLICATIONS

Jostensen et al., FEMS Microbiology Letters, vol. 151, No. 1, pp. 95–101, 1997.*

* cited by examiner

*Primary Examiner*—Francisco Prats
*Assistant Examiner*—Susan D. Coe
(74) *Attorney, Agent, or Firm*—Madson & Metcalf

(57) ABSTRACT

The present invention relates to Pseudomonas sp. YS-180 having a capability of producing a docosahexaenoic acid and a method for the production of DHA using such a microorganism. Pseudomonas sp. YS-180 was isolated and identified from the intestine of fishes by investigating the morphological, culturing, and physiological characteristics of a strain excellent in a DHA-producing capability. By TLC and GC, Pseudomonas sp. YS-180 according to the present invention was confirmed that it produced the greatest amount of DHA when it was shaking-cultured in a culture containing glucose 2% (w/v), a yeast extract 2% (w/v), and sea water 20%(v/v). Optimal conditions for producing DHA were a pH of 6.0, and a temperature of 20° C. Under these conditions a DHA production was 96.7 mg/L, and a biomass growth was 7.8 g/L.

3 Claims, 6 Drawing Sheets

METHOD FOR PRODUCING DOCOSAHEXAENOIC ACID (DHA) USING PSEUDOMONAS SP. YS-180

BACKGROUND OF THE INVENTION

1. Field of the Invention

The present invention relates in general to Pseudomonas sp. YS-180 having a capability of producing docosahexaenoic acid (hereinafter called "DHA") and a method for the production of DHA using such a microorganism. More particularly, the present invention relates to a method comprising screening, from intestines of fish, a microbial strain, Pseudomonas sp. YS-180, that effectively produces DHA, as one of its unsaturated fatty acids, investigating the morphological, culturing and physiological characteristics of the screened strain to isolate and identify, and establish optimal conditions for the production of DHA.

2. Description of the Prior Art

DHA is an unsaturated fatty acid that has been of keen interest since an epidemiologic survey employing Eskimos as subjects of the survey at the 1970's. This is associated with phospholipids, such as phosphatidyl ethanolanine (PE) and phosphatidyl serin (PS), present in the grey matter of the human frontal lobe, while having inherent physiological functions connected with the brain and retina. In addition, DHA is highlighted as a health food due to various efficacies, such as anti-trombus, antihypersensitive, anti-arrhythmic, and anti-camcer properties. However, DHA is not easy to synthesize chemically, and thus, it is currently obtained from natural material. Till now, such a highly unsaturated fatty acid has been industrially extracted from oils of fishes having a blue back, such as mackerel, saury, bluefin tuna, horse mackerel, and herring.

Fish oil fatty acids often originate from marine microorganisms, such as algae and vegetable plankton, which are ingested by such fish. However, it is problematic in that DHA extracted from the fish oil is unsuitable for the use as foods and medical supplies when the fish is contaminated with an environmental pollution material. Another problem is that it is difficult for DHA to be produced in a stable way. Additionally, another problem is that DHA has an offensive fish odor. Consequently some researchers have predicted that, in addition to being present in fish oil, DHA-producing strains could be also present in the intestine of the fishes having the blue back. Therefore, bacteria isolated from an intestine of a variety of fishes and marine animals were cultured and examined for a DHA-producing capability. As a result, many kinds of DHA-producing strains wvere isolated. Marine microorganisms reported producing EPA and DHA, simultaneously include *Isochrysis galbana,* Dinoflagellate sp. and *Crypthecodinium cohnii* of Chrysophyceas genus.

There are current investigations to produce EPA and DHA from bacteria or algae in large quantities using biotechnology. Examples ofthese studies include Watanabe et al., "a fatty acid composition of an EPA product from marine bacteria", J. Mar. Biotechnol., 4, 104–112, 1996; Baumann et al., "a possibility to produce EPA from novel microorganisms of the South Pole", Int. J. System, Bacteriol., 47, 1040–1047, 1997 Bico et al., "fatty acids from marine plants", Phytochemistry, 34, 1521–1533, 1993; PCT publication WO 91/11918 (1991) concerning a DHA production; Yamajaki, "a production and use of EPA by marine bacteria", Bio Industry., 6, 491–501, 1989; and Kazo et al. "Composition of fatty acids and lipids of a novel DHA product" Lipids. 32, 9 p. 975–978, 1997. However, these studies are only basic investigations concerning the production of DHA and EPA from microorganisms.

SUMMARY OF THE INVENTION

It is therefore an object of the present invention to screen a strain excellent in its production capacity of DHA, a useful unsaturated fatty acid, from the intestine of fish, investigate the morphological, culturing, and physiological characteristics of the screened strain, isolate and identify Pseudomonas sp. YS-180, and establish optimal conditions for producing DHA.

BRIEF DESCRIPTION OF THE DRAWINGS

Other objects and aspects of the invention will be apparent from the following description of embodiments with reference to the accompanying drawings, in which.

DETAILED DESCRIPTION OF THE PREFERRED EMBODIMENTS

The foregoing and other objects, features and advantages of the invention will be apparent to those skilled in the art to which the present invention relates from reading the following specification.

The present invention comprises isolating a DHA-producing, strain from the intestines of fishes, and identifying the isolated strain to grasp effects of temperature, pH, a glucose concentration, a yeast extract, and sea water on the production of DHA, extracting total lipid from a product, and analyzing a content of DHA.

Isolation and identification of YS-180, a DHA-producing strain.

Figure 1:
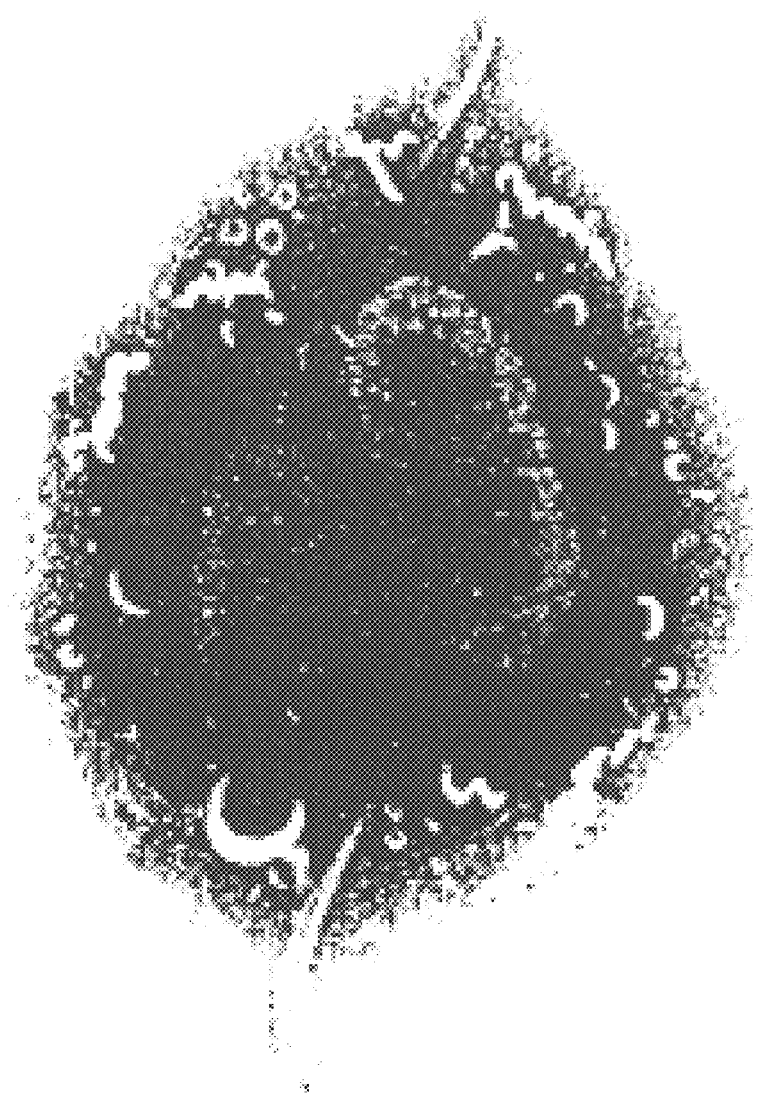
FIG. 1 is an electron microscope of a strain, Pseudomonas sp. YS-180 in accordance with the present invention.

Pseudomonas YS-180 isolated from the intestine of a cuttlefish had the form of a straight rod of a gram negative. Also, it was free of spores, and had a motility. As shown in FIG. 1, this had a plurality of polar flagellas and a light creamy punctiform. Thus, this was regarded as a Pseudomonas genus.

Culturing and physiological characteristics of the isolated strain are shown in Table 1 below and compared to a Bergey's manual of systematic bacteriology. As clear from Table 1, the isolated strain was gyrown at a temperature of 4 to 40° C. and a pH of 5 to 12, and could be grown even at a NaCl concentration of 9% or less. This strain exhibited catalase, oxidase, and lipase activities. Starch and cellulose could not be hydrolyzed, whereas casein was hydrolyzed. Moreover, $NH_3$ was produced from arginine and peptone, respectively, and citrate was used. Additionally, sugars, such as arabinose, cellobiose, dextrin, and galactose, could be used, whereas cellulose, glycerol, and inositol could not be used. From such results, the strain in accordance with the present invention was identified as Pseudomonas genus, and therefore named "Pseudomonas sp. YS-180".

This strain was deposited at the Korean Culture Center of Microorganisms in Korean Federation Treaty on Apr. 14. 1999 under an accession number of KCCM 10157.

TABLE 1

Morphological and physical characteristics of Pseudomonas YS-180

| Growth characteristics | Growth conditions |
|---|---|
| Growth temperature | 4 to 40° C. |
| Growth pH | 5 to 10 |
| Obstruction conc. of NaCl | ≦9% |
| Catalase | + |
| Oxidase | + |
| Nitrase | − |
| Lipase | + |
| Arginine dihydrolase | + |
| Starch hydrolysis | − |
| Casein hydrolysis | + |
| Cellulose hydrolysis | − |
| Indole production | − |
| Levan formation from sucrose | − |
| $NH_3$ production from arginine | + |
| $NH_3$ production from peptone | + |
| Utilization of citrate | + |
| Methyl red test | + |
| Voges-Proskauer reaction | − |
| Nitrate reduction | − |
| Denitrification | + |
| Hemolysis | + |
| O-F test | − |
| $H_2S$ production | Oxidation |
| Gelatine hydrolysis | + |
| Utilization of sugar | + |
| Arabinose | + |
| Cellobinose | + |
| Cellulose | − |
| Dextrin | + |
| Fructose | + |
| Galactose | + |
| Glucose | + |
| Glycerol | − |
| Inositol | − |

*+: Positive
−: Negative

Extraction of total lipid.

A biomass collected by a centrifugation was suspended in an extracting solvent of chloroform and methanol (2:1, v/v) and homogenized for 5 minutes. Then, the homogenized biomass was centrifuged at 15,000 rpm for 10 minutes and a chloroform layer at the lower portion was carefully isolated. After that, the isolated layer was concentrated under a reduced pressure and subjected to an extraction.

Analysis of a DHA content.

DHA was quantitatively analyzed according to an AOAC method. An extracted fatty acid was saponified according to the conventional method and esterified with $BF_3$-methanol. The fatty acid was analyzed by TLC (n-hexane:ether=18:1) and Gas Chromatography (capillary column 0.24×3 m, FID Shimadzu, Japan) to identify DHA. In this analysis, a column temperature was raised from 150° C. to 240° C. at a rate of 3□/minute, and nitrogen was used as a carrier gas at a passing rate of 1.5 ml/minute.

The following examples are for illustration purposes only and in no way limit the scope of this invention.

Example 1

A DHA-producing strain isolated from the intestine of a cuttlefish was suspended in sterilized seawater. Then, a PYM-glucose solid culture comprising peptone 1.04%, a yeast extract 0.50%, a meat extract 0.25%, glucose 2.0%, and sea water 50%, pH 7.0, was spread onto a plate culture and then cultured at a temperature of 20° C. for three days. Thereafter, each colony was inoculated into the same liquid culture and shaking-cultured at a temperature of 20° C. for three days. Next, after the resulting culture was centrifuged for 10 minutes, a biomass was collected. Then, lipid was extracted and a strain was isolated having an excellent DHA-producing capacity.

Figure 2:
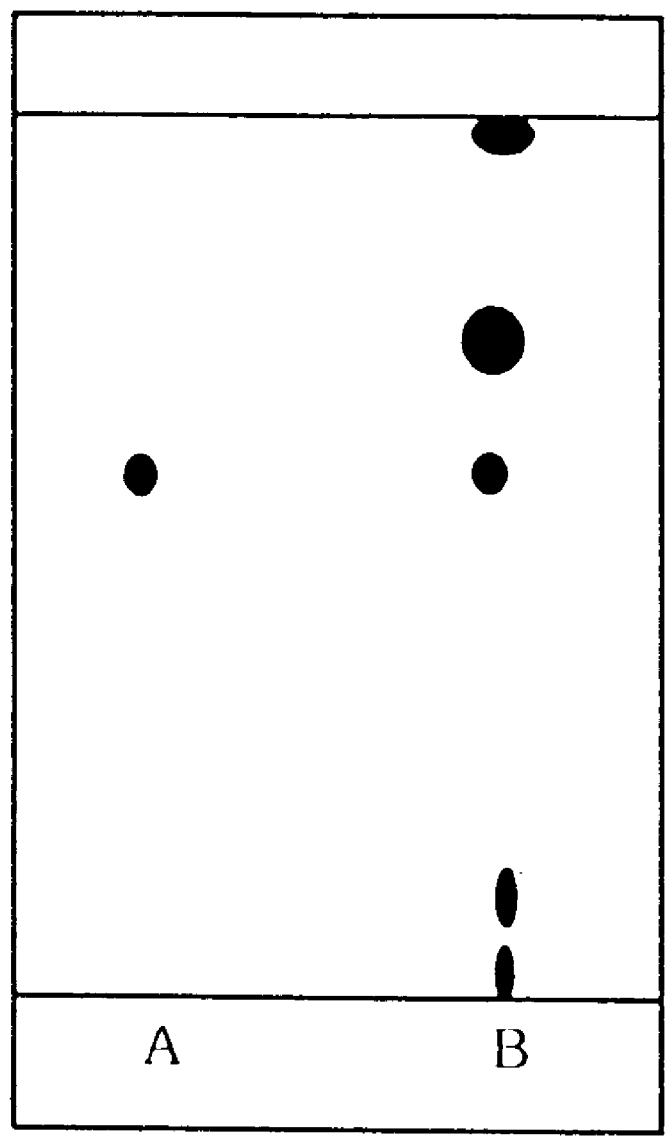
FIG. 2 shows an Rf value of TLC for DHA sample (A) cultured using a strain according to the present invention, as compared with that for the standard sample (A)
Figure 3:
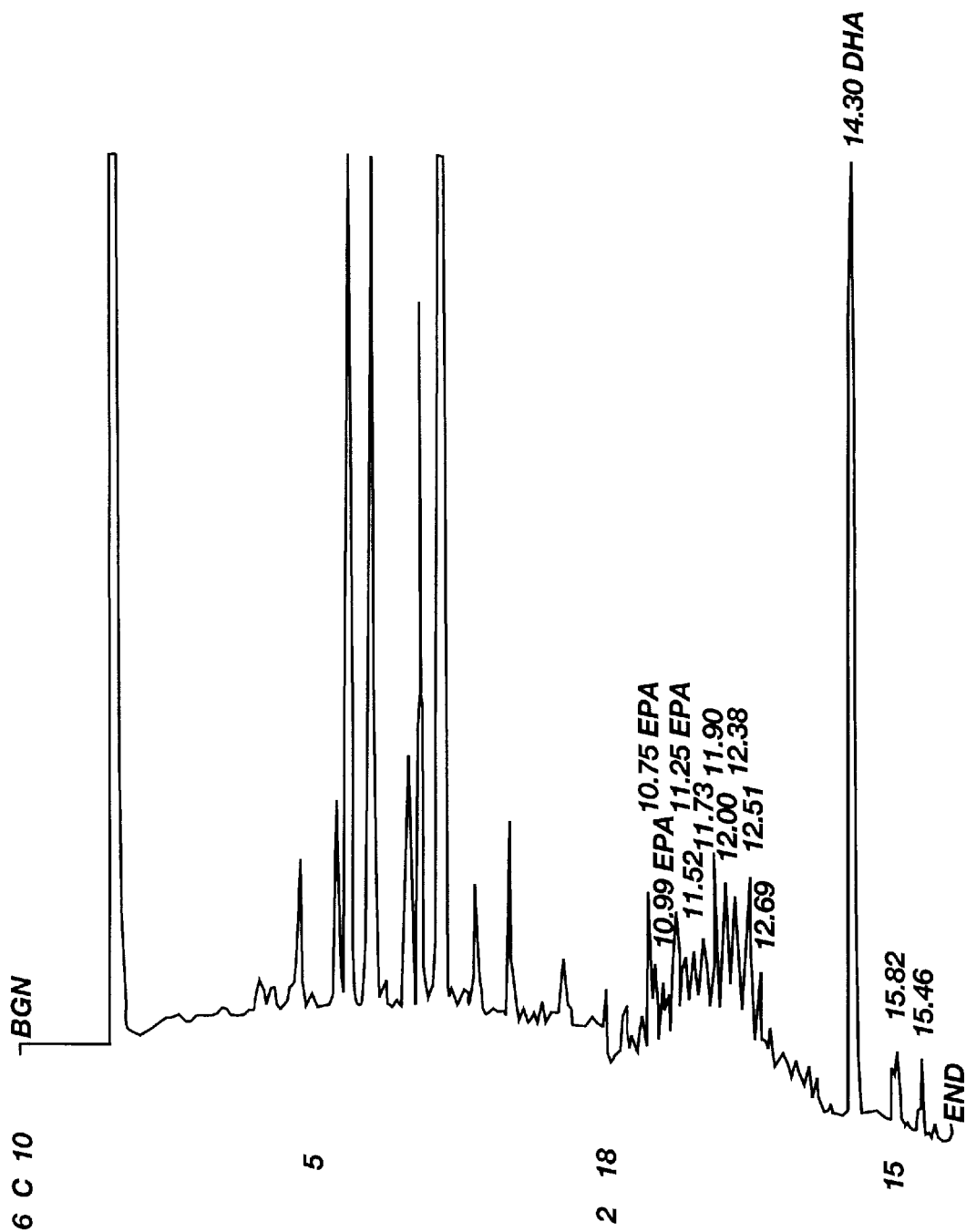
FIG. 3 shows a gas chromatogram of a fatty acid obtained by culturing a strain of the present invention in PYM-glucose medium.

DHA extracted from Pseudomonas sp. YS-180 along with a standard DHA, were developed in a developing solvent. As a result, DHA extracted from Pseudoinonas sp. YS-180 has shown a Rf value of 0.66 that is equal to that of the standard DHA, as shown in FIG. 2. In addition, an analysis of DHA by gas chromatography indicated a single peak at a retention time of 14 and one half minutes, as shown in FIG. 3. A content of DHA in the fatty acid was 35.77%.

Figure 4:
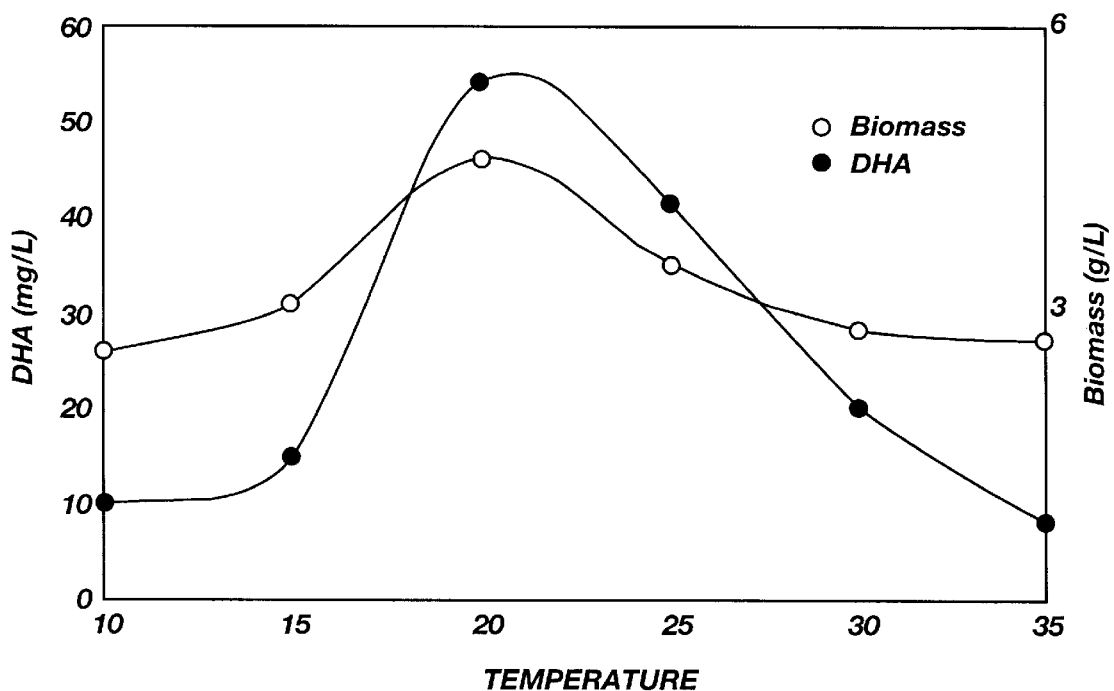
FIG. 4 shows an effect of temperature on a DHA production and a biomass growth by a strain according to the present invention.

Results examined for an effect of the culturing temperature on the production of DHA are shown in FIG. 4. As clear from FIG. 4, the DHA content and the growth of the biomass were maximum values at a temperature of 20° C., whereas the growth of the biomass was rapidly decreased at a temperature of 25° C. or above.

Figure 5:
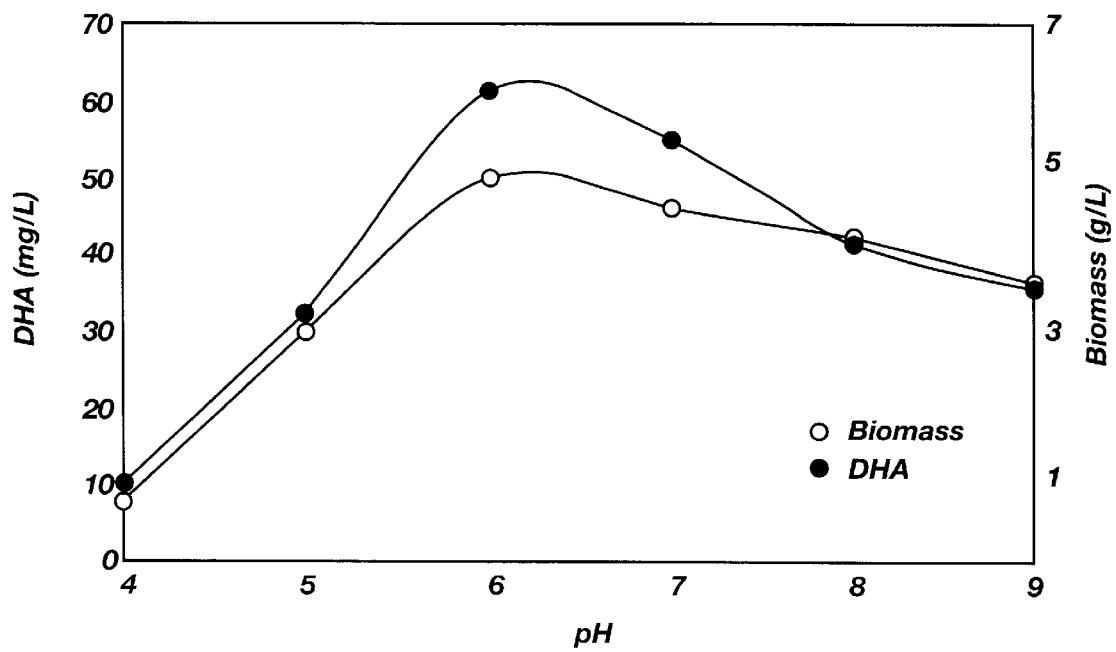
FIG. 5 shows an effect of an initial pH on a DHA production and a biomass growth by a strain according to the present invention.

Results analyzed for an effect of an initial pH on the production of DHA are shown in FIG. 5. As clear from FIG. 5, the DHA content and the growth of the biomass were maximal at an initial pH of 6, whereas rapidly decreasing at a pH of 5 or below and a pH of 9 or above.

Results analyzed for an effect of a variety of carbon sources on the production of DHA are shown in Table 2 below. As evident from Table 2, the use of glucose as the carbon source exhibited the highest DHA-producing capability as 61.3 mg/L, and the use of starch as the carbon source shown a DHA-producing capability of 53.4 mg/L.

TABLE 2

DHA-producing capability by Pseudomonas sp. YS-180 varying depending on carbon source

| Carbon source | Biomass(g/l) | DHA(mg/l) |
|---|---|---|
| Fructose | 1.1 | 7.2 |
| Sucrose | 1.5 | 11.5 |
| Glucose | 5.0 | 61.3 |
| Starch | 4.9 | 53.4 |
| Lactose | 1.1 | 13.7 |

Figure 6:
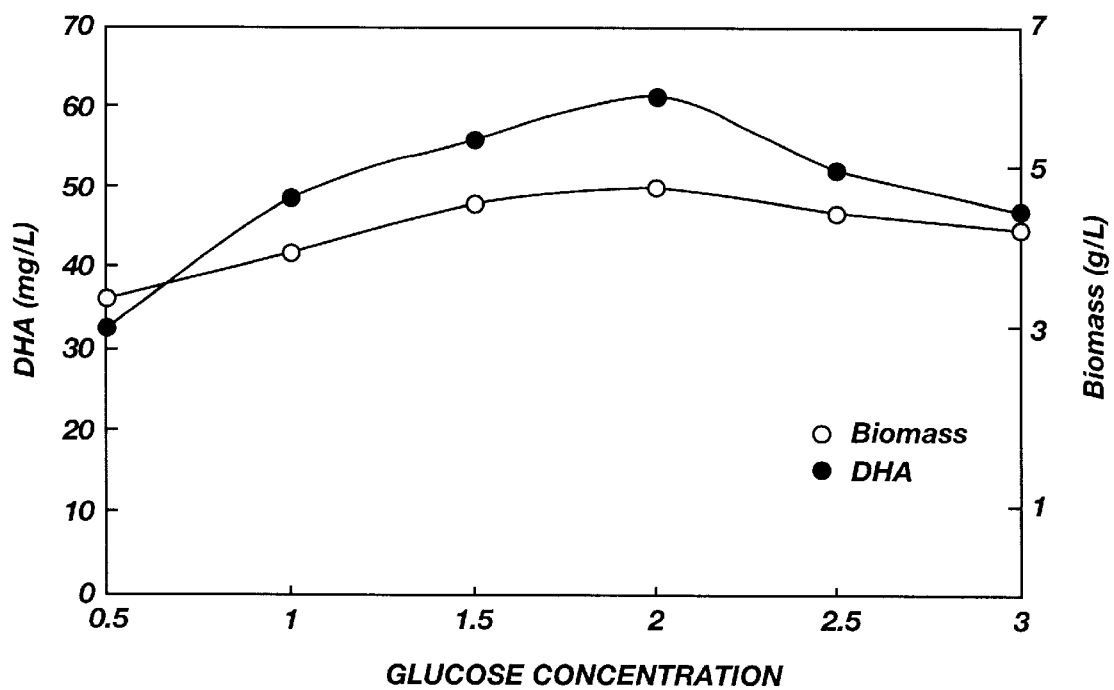
FIG. 6 shows an effect of a glucose concentration on a DHA production and a biomass by a strain according to the present invention.

Furthermore, results analyzed for a glucose concentration are shown in FIG. 6. As apparent from FIG. 6, the addition of glucose at 20% concentration exhibited the highest DHA-producing capability.

Results analyzed for an effect of a variety of organic nitrogen sources on the production of DHA are shown in Table 3 below. As clear from Table 3, the use of a beef extract, peptone, triptone and a yeast extract resulted in DHA-producing capabilities of 24.0 mg/L, 20.7 mg/L, 34.0 mg/L, and 61.3 mg/L, respectively.

TABLE 3

DHA-producing capability by Pseudomonas sp. YS-180 varying depending on nitrogen source

| Nitrogen source | Biomass (g/l) | DHA (mg/l) |
| --- | --- | --- |
| Beef extract | 4.3 | 24.0 |
| Corn steep liquor | 2.1 | 10.5 |
| Malt extract | 1.0 | 6.0 |
| Peptone | 2.5 | 20.7 |
| Soybean meal | 0.8 | 7.6 |
| Triptone | 3.5 | 34.0 |
| Yeast extract | 5.0 | 61.3 |
| Urea | 3.2 | 27.4 |

Figure 8:
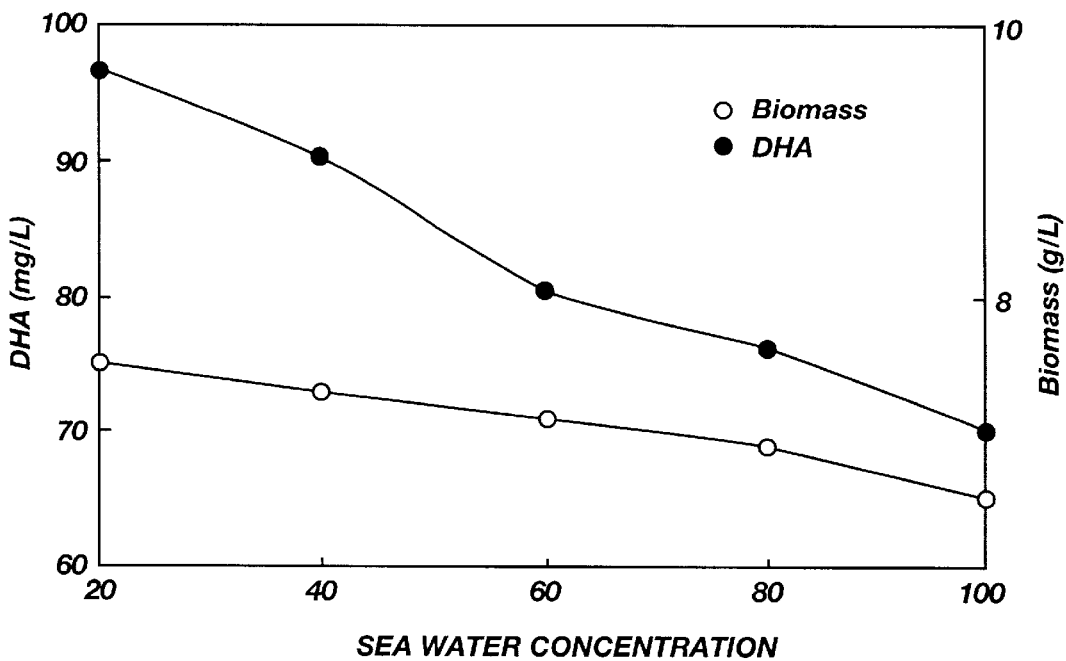
FIG. 8 shows an effect of sea water on a DHA production and a biomass growth by a strain according to the present invention.

Results analyzed for an effect of seawater on the production of DHA are shown in FIG. 8. As apparent from FIG. 8, the use of seawater at a concentration of 20% (v/v) exhibited the highest DHA-producing capability as 96.7 mg/L. At a seawater concentration exceeding 20%(v/v). the DHA-producing capability was gradually decreased.

Figure 9:
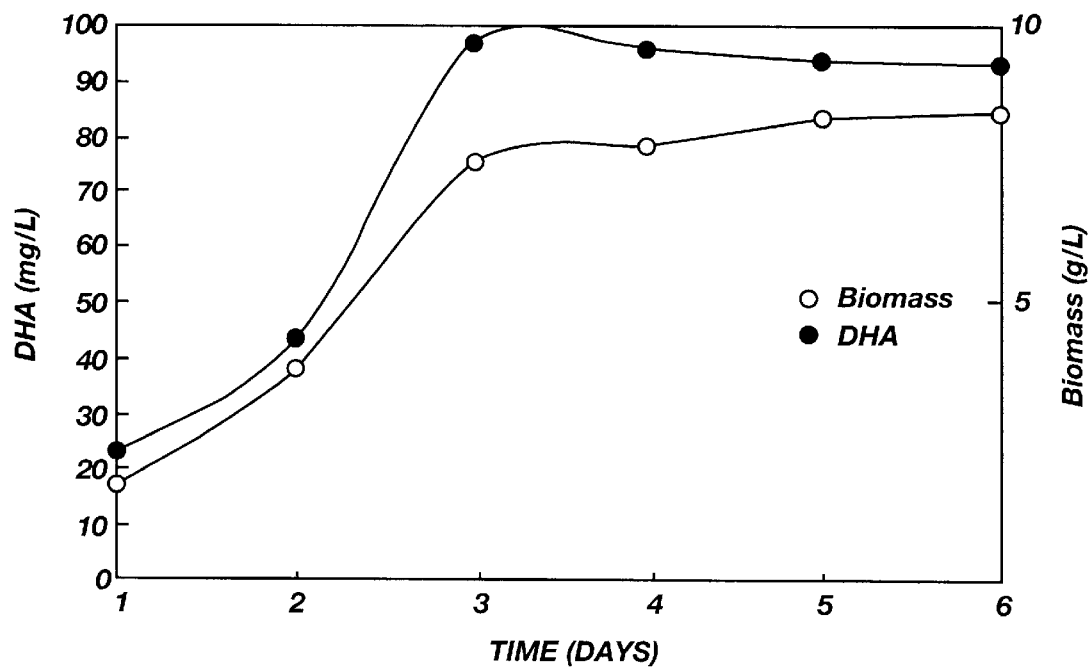
FIG. 9 shows an effect of a biomass growth time on a DHA production and a biomass growth by a strain according to the present invention.

Effects of a culturing time on the DHA production by Pseudoimonas sp. YS-180 were longitudinally examined using an optimal culture. Results are shown in FIG. 9. As shown in FIG. 9, the DHA production was the highest at 96.7 mg/L at 3 days after culturing. Moreover, alter culturing for 3 days, the biomass production was increased by about 1.5 times from 4.6 g/L to 7.8 g/L, while the DHA content was increased be about 2 times from 54.9 mg/L to 96.7 mg/L.

Figure 7:
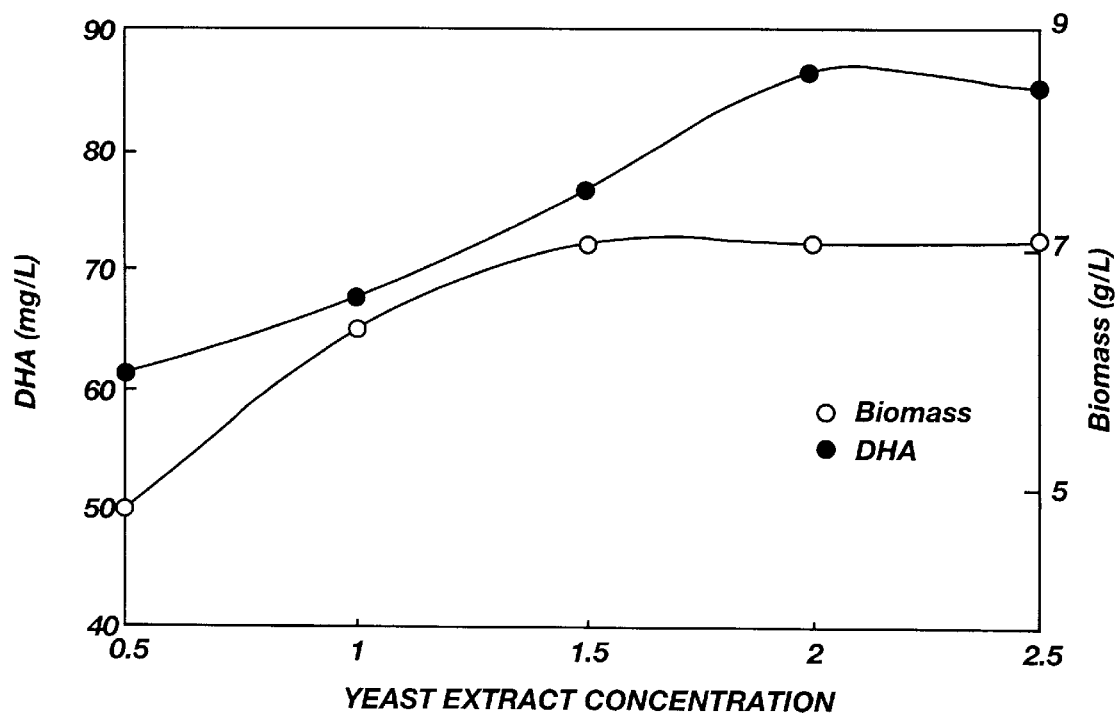
FIG. 7 shows an effect of a yeast extract on a DHA production and a biomass growth by a strain according to the present invention.

Results analyzed for an effect of a yeast extract concentration on the production of DHA are shown in FIG. 7. As evident from FIG. 7, the addition of the yeast extract at 2% concentration exhibited the highest DHA-producing capability as 86.4 mg/L.

Example 2

A culture including peptone 1.04%, a yeast extract 0.5%, a meat extract 25%, glucose 2.0%, and sea water 50% was sterilized in an autoclave, adjusted to pH 7.0, inoculated with Pseudomonas sp. YS-180, a DHA-producing strain, and incubated at a temperature of 20° C. for three days. Thereafter, each colony was inoculated into the same liquid culture including a yeast extract 2.0%, peptone 1.04%, triptone 0.25%, glucose 2.0% and sea water 20%, and shaking-cultured at a temperature of 20° C. for three days. Next, after the resulting culture was centrifluged at 1.500 rpm for 10 minutes, a biomass was collected. Then, lipid was extracted, and 96.7 mg/L of DHA was obtained.

As apparent from the above description, DHA was obtained in a high yield by incubating the culture inoculated with Pseudomionas sp. YS-180 strain isolated according to the present invention, at a neutral pH for 3 to 6 days. DHA so obtained is an unsaturated fatty acid, and has a great effect in preventing adult diseases, such as a high blood pressure, and an arterial sclerosis, etc. Thus, DHA produced in accordance with the present invention can be widely applied to fields, such as foods, medical supplies, and feeds.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A Pseudomonas sp. YS-180 strain isolated from the intestine of fishes and producing docosahexaenoic acid (DHA).

2. A method for producing docosahexacnoic acid (DHA) comprising the steps of:
    inoculating a culture wvith the strain of claim 1: and
    incubating the resulting culture at a pH of 6.0 to 7.0 and a temperature of 20 to 25° C. for 3 to 6 days.

3. The method according to claim 2, in which the culture comprises peptone 0.5 to 1.5% (w/v) a yeast extract 0.5 to 2.0% (w/v), a meat extract 0.25 to 0.5 % (w/v), glucose 1.0 to 3.0% (w/v), and sea water 20 to 50% (w/v).

* * * * *